(12) United States Patent
Hagele

(10) Patent No.: US 6,197,008 B1
(45) Date of Patent: Mar. 6, 2001

(54) PRECISE INSTILATION EYE DROPPER TIP

(76) Inventor: James Hagele, 13262 Evergreen Dr., Nevada City, CA (US) 95959

( * ) Notice: Subject to any disclaimer, the term of this patent is extended or adjusted under 35 U.S.C. 154(b) by 0 days.

(21) Appl. No.: 09/320,163

(22) Filed: May 26, 1999

(51) Int. Cl.[7] .................................................. A61M 35/00
(52) U.S. Cl. ........................................... 604/295; 222/420
(58) Field of Search .................................... 604/294–302; 222/211, 420

(56) References Cited

U.S. PATENT DOCUMENTS

| | | | |
|---|---|---|---|
| 2,728,491 | * 12/1955 | Aneshansley | 222/420 |
| 2,734,665 | * 2/1956 | Flamm | 604/294 |
| 3,756,478 | * 9/1973 | Podell et al. | 222/420 |
| 5,373,964 | * 12/1994 | Moore | 222/420 |
| 5,431,314 | * 7/1995 | Bonnelye et al. | 222/420 |
| 5,588,559 | * 12/1996 | Vallet Mas et al. | 604/295 |
| 6,041,978 | * 3/2000 | Hagele | 604/294 |

* cited by examiner

Primary Examiner—John G. Weiss
Assistant Examiner—David J. Cho

(57) ABSTRACT

A dropper tip 30 is provided which allows a person to instill a drop D into and eye E from a bottle 20 that has compressible and resilient walls 19 while the bottle 20 is held in a horizontal orientation.

The dropper tip 30 includes an internal passage 37 into which a stem 35 is inserted. The stem 35 has a groove 36 along its peripheral surface which allows the flow of liquid 21 from the reservoir 20 to the free end 29 of the tip 30. The stem 35 protrudes from the external opening 44 of the internal passage 37 of the tip 30 and has a head 33 on the protruding end. The drop D adheres to the head 33 rather than adhere to and migrate along the external surface 28 of the tip 30.

The dropper tip 30 further includes an annulus 32 at the free end 29 of the tip 30 which encircles the external opening 44 of the internal passage 37. The annulus provides a surface for a drop D of liquid 21 to adhere to while awaiting release.

The dropper tip 30 further includes a fissure 34 at the free end 29 of the tip 30 which provides an area for drop formation and retention and also acts as a guide to direct the falling drop D into an eye E while the bottle 30 is held horizontally.

8 Claims, 3 Drawing Sheets

PRECISE INSTILATION EYE DROPPER TIP

FIELD OF INVENTION

This invention relates to an eye dropper tip that enables drops of liquid to fall precisely and consistently from its free end, even if the tip is held in a horizontal orientation, rather than adhere to and migrate along the external surface of the tip.

BACKGROUND OF THE INVENTION

The instillation of medicinal eye drops tends to be difficult and annoying for many individuals. Generally, a person tilts their head back and looks up. Simultaneously, the dropper bottle is elevated above and over the eye and the walls of the bottle are compressed, causing the drop to fall toward the eye.

Often, however, the drop misses the eye altogether and falls on the face, where it has no therapeutic value and may even be irritating to the skin. Or, several drops might be released if there is a momentary delay in the first drop and a second one is squeezed from the bottle, causing an overdose and waste of medicine.

The standard eye dropper tips that are currently being used, require that the bottle be held in a near vertically down position. This is necessary to make certain the drop falls from the end of the tip rather than adhere to the tip's external surface. The more vertically down the tip is held, the more likely the drop will fall from the end of the tip rather than adhere to and migrate along the external surface of the tip.

Once a drop does adhere to the external surface of the tip and refuses to fall, it attracts another drop because of molecular cohesive and adhesive forces. This is a result of surface tension. When the bottle and tip are held in a less vertically down orientation and in a more near horizontal position, some three or even four drops can be observed to adhere to each other and to the external surface of the tip rather than fall. The forces of cohesion and adhesion at times can be greater than the force of gravity acting upon the drop. When this happens, the drop(s) will continue to adhere to the surface of the dropper tip and migrate along its surface where a portion of the liquid will eventually fall from the base of the tip or even from the threaded portion of the bottle. One can readily see the amount of waste and the poor placement of the falling drop(s) that results. This may also cause a greater or a lesser dosage of medication to eventually fall into the eye, depending on the size of the drop.

There are several factors that often complicate the conventional way of instilling eye drops. First, it is difficult for some individuals, especially the elderly, to elevate their shoulder high enough to place the eye dropper in an ideal position above the eye. Secondly, limitation of motion of the hand or the wrist makes it difficult to turn the bottle in a substantially inverted position. Thirdly, some individuals, as they grow older, find that their hands and head are no longer steady, thus posing the problem of not being able to maintain proper alignment while the drops are being instilled. It is interesting that many patients, even without these limitations, confess that they are never sure where the drop will fall, even though they use drops on a regular, daily basis.

There are some persons who are unable to administer their own drops and either rely on a spouse or a caregiver to instill them. Often the caregiver finds it difficult to get the patient to open their eyes widely while the drops are being instilled. When the hand of the assistant comes in front of the eye, holding the bottle vertically down and obscuring the vision, there is a very strong protective reflex to close the eyelids. This makes it difficult to instill the drops with any accuracy and often the drop misses the eye and runs down the cheek. At that point one doesn't know if a drop or a portion of a drop did indeed get into the eye.

The vast majority of individuals administer their own drops and it is imperative to devise a better delivery system for the benefit of these individuals. It is important that the condition for which the drops are taken is adequately treated and that waste is kept to an absolute minimum.

Billions of dollars are spent annually just to treat glaucoma. It is obvious that a significant amount of these dollars are wasted because of the present delivery system for these medications. Presently, insurance companies, health maintenance organizations, governmental programs and especially patients themselves are concerned about the cost of treating various medical conditions. It is essential that the delivery system for ocular medications be reexamined and improved.

It has been observed that a commonly used anti-glaucoma medication in a 2.5 ml (milliliters) bottle on the market today, will release about 105 drops when the bottle is held in a vertically down position. However, when the bottle and tip is held down approximately 10 to 15 degrees, which is frequently the angle that individuals hold the dropper, only about 75 drops can be made to fall from the end of the dropper tip. The rest of the liquid tends to adhere to the outer surface of the tip and roll down the dropper tip toward its base and onto the bottle itself. It is obvious that there is considerable waste and a lack of accuracy in the instillation of drops into an eye with the present delivery system.

Once a drop adheres to the external surface of the dropper tip rather than fall, further drops released from the tip will continue to adhere to each other and to the surface of the tip. These drops will migrate along the external surface of the tip. There will always be a portion of this liquid that does not fall and when the cap is placed on the bottle, this liquid adheres to and dries out on the inside of the cap and on the outside of the bottle. This accounts for the dried-out material that is often found on both the internal threads of the cap and the external threads of the bottle after the bottle has been used up.

Not only is an improved dropper tip needed, but an improved dropper bottle to complement such a tip is mandatory. Most dropper bottles made and used today, must also be held in a near vertically down position to get the last third of the liquid in the bottle to flow to the tip where it can be expressed in drop form.

(A dropper bottle to complement the present invention has been designed that makes drop instillation more accurate, consistent and simultaneously permits the patient to hold the dropper bottle and dropper tip in a near horizontal orientation when the drop is released into an eye. A patent for such a newly designed bottle has been filed with the U.S. Patent and Trademark Office; Titled, "Precision Release Eye Dropper Bottle"; Inventor, James Hagele; PTO Application No., 09/272,066; Filing Date, Mar. 16, 1999; Preliminary Class, 604.)

SUMMARY OF THE INVENTION

The present invention addresses the problems associated with placing a drop into an eye in a consistent and precise manner and with minimum waste. A dropper tip that allows the patient to hold the bottle in a near horizontal orientation as the drop is released into an eye has been designed. The dropper tip enables a drop to fall from the free end of the tip rather than adhere to and migrate along the external surface of the tip. This is permitted even though the bottle is not held in a vertically down position as required by today's standard dropper tips.

The dropper tip is especially helpful to those individuals who have restricted movments of the shoulder, the hand, or the wrist. In those cases the rotation of the wrist to place the tip in a markedly down position is not required. Also the shoulder need not be elevated so high in order to place the tip and the bottle in a vertically down position as is now required. Rather, the person instilling the drop can hold the tip above the eye and align the end of the tip with the eye while releasing the drop without the shoulder, wrist, and hand movements that are required with the standard eye dropper tips that are used today.

For those individuals who are unable to administer their own drops and must rely on someone else, the present invention is of great help. The outer lower eyelid of the eye is retracted down and out by the caregiver, creating a small pocket in the lower eyelid. The tip of the present invention is brought up from the side of the face and held in a near horizontal orientation below the line of vision of the patient while the drop is made to fall from the end of the dropper tip into this created pocket. This method is much less threatening to the patient than holding the bottle and tip vertically in front of the eye. Usually, if done quickly and properly, the patient will hardly know the drop was instilled.

The dropper tip of the present invention, when combined with an improved bottle, can be used in another way by those individuals who find it hard to instill drops into an eye with the conventional methods. It also can be of great help for those individuals, usually the elderly, who no longer have a steady hand or steady head. This method permits the bottle to be grasped by the fingers and thumb and rested on the bridge of the nose while the dropper tip is held over the eye. Once in position, the walls of the bottle are compressed, causing the drop to fall directly into the eye. Since the dropper tip has been designed to not permit the drop to adhere to and migrate along the external surface of the dropper tip when held horizontally, the drop can be made to fall into the eye from the free end of the tip. This is a much easier approach for applying drops to the eyes when compared to the conventional method of holding the bottle over and above an eye.

The present invention of a "Precise Instillation Eye Dropper Tip" has been designed to solve the common problems of instilling drops of liquid into an eye. The drop is made to fall from the free end of the tip rather than adhere to and migrate along the external surface of the tip. Also, the present invention guides the drop as it falls from the free end of the tip by a specially designed combination of a stem and head, an annulus and a fissure, all for drop formation and guidance. All these unique features add up to precisely and consistently instilling a drop of liquid into an eye while the dropper tip and the bottle are held in a more horizontal orientation. This control of drop formation and instillation can reduce the amount of waste and cost to the patient.

The present invention may also be used for dispensing liquids other than those that are instilled directly into the eye. Individuals wearing contact lenses would greatly benefit from the present invention if the dropper tip was utilized on the present contact lens solution bottles. These include wetting, cleaning, soaking, and multiple purpose solutions, all of which are used in the care of contacts. If one observes these bottles of solutions being used, it is obvious that drops of liquid adhere to and migrate along the external surface of the dropper tip when the bottle is held in a more horizontal orientation over the contact lens. It is not only a matter of waste but also a problem of accuracy in having the drop(s) fall on the intended target.

OBJECTS OF THE INVENTION

A primary object of the present invention is to provide a dropper tip that enables a drop of liquid to fall precisely and consistently from the free end of the tip.

Another object of the present invention is to provide a dropper tip that prevents a drop of liquid from adhering to the external surface of the tip rather than falling.

Another object of the present invention is to provide a dropper tip that prevents migration of the drop along the external surface of the tip rather than falling.

Another object of the present invention is to provide a dropper tip that guides the drop as it falls toward a person's eye.

Another object of the present invention is to provide a dropper tip that reduces waste.

Another object of the present invention is to provide a dropper tip that controls the timing of the release of the drop.

Another object of the present invention is to provide a dropper tip that helps to maintain a consistency in the size of the drop.

Another object of the present invention is to provide for a dropper tip that can be held in a near horizontal orientation by an individual with restricted hand, wrist and shoulder movements and and still have the drop fall from the free end of the tip.

Another object of the present invention is to provide for a dropper tip configured to be used with a bottle that is supported against the bridge of the nose for those individuals with an unsteady hand or head.

Another object of the present invention is to provide for a dropper tip whereby a caregiver can place a drop into a person's eye while holding the tip to the side and below the line of vision in a horizontal orientation.

Another object of the present invention is to provide for a dropper tip that can be used for contact lens solution bottles to prevent waste and give better control in the placement of the liquid on the contacts.

Other further objects of the present invention will become apparent from a careful reading of a background of the invention, a summary of the invention, a detailed description of the invention, the drawings, and the claims.

DESCRIPTION OF PREFERRED EMBODIMENT

Figure 1:
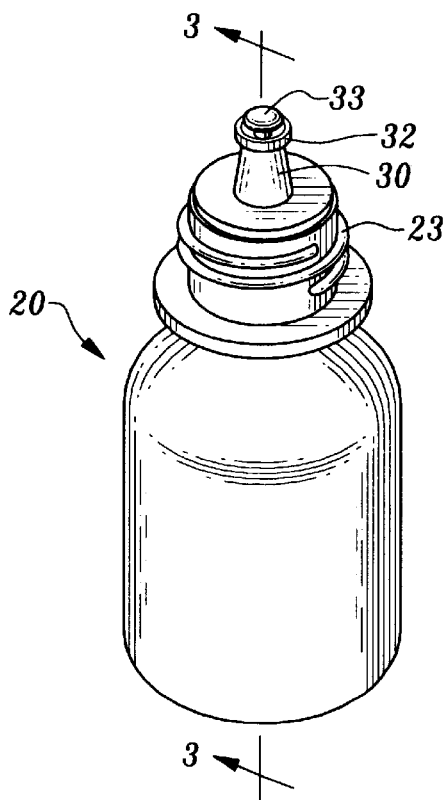
FIG. 1 is a perspective view of an assembled bottle with the present invention.
Figure 2:
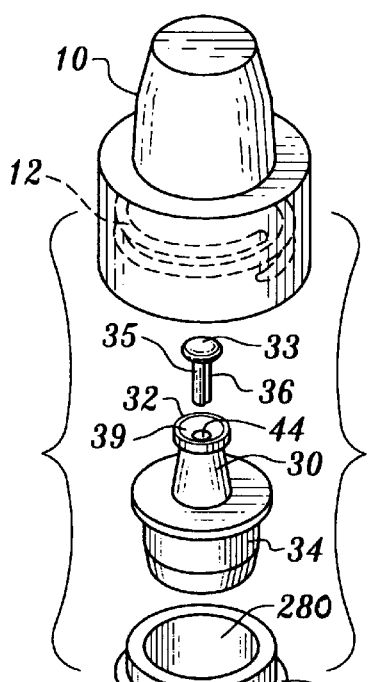
FIG. 2 is an exploded perspective view of a bottle with the present invention.
Figure 3:
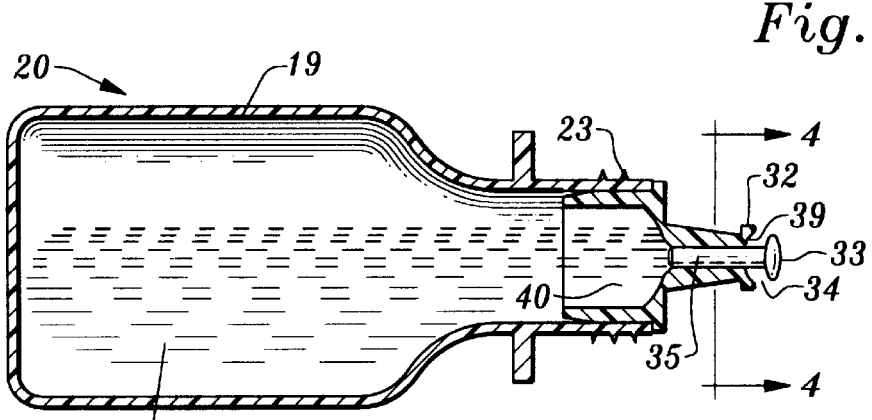
FIG. 3 is a sectional view 3—3 of FIG. 1 of a bottle with the present invention.

Referring to the drawings where like reference numerals represent like parts throughout the various drawing figures, reference numeral 30 (FIGS. 1, 2, 6) is directed to a dropper tip for instilling a drop D of liquid 21 into a person's eye E. The most preferred embodiment dropper tip 30 consists of a hollowed-out 40 base 34 (FIG. 6) which inserts into an opening 280 (FIG. 2) of an eye dropper bottle 20. The reservoir walls 19 of the bottle 20 are resilient and compressible (FIG. 3).

Figure 4:
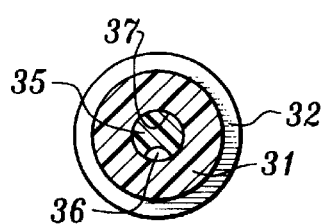
FIG. 4 is a cross sectional view 4—4 of FIG. 3 looking from the reservoir end toward the free end of the tip of the preferred embodiment of the groove of the stem of the present invention.
Figure 5:
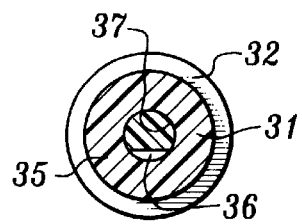
FIG. 5 is a cross sectional view 4—4 of FIG. 3 looking from the reservoir end toward the free end of the tip of the most preferred embodiment of the groove of the stem of the present invention.
Figure 6:
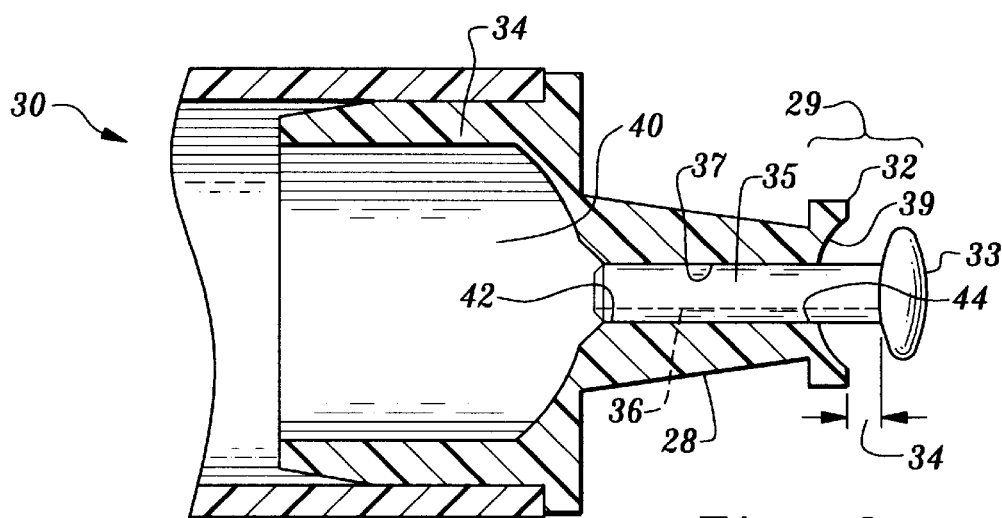
FIG. 6 is a detailed cross sectional view of the present invention.

The dropper tip 30 further includes an internal passage 37 (FIGS. 6 and 6A) into which a stem 35 is inserted. The internal passage 37 is surrounded by the internal walls 31 of the tip 30 (FIGS. 4 and 5). The stem 35 fits securely into the internal passage 37 and protrudes at the free end 29 of the dropper tip 30. The stem 35 has a groove 36 running along its peripheral surface. The groove 36 provides a channel for the liquid 21 to flow from the reservoir 20 out the free end 29 of the tip 30 in drop D form. The groove 36 may be curved (FIG. 4) or it may be flat (FIG. 5). The size of the groove 36 determines the volume of liquid 21 that flows from the reservoir 20 out the free end 29 of the tip 30. The dropper tip 30 further includes a head 33 on the protruding stem 35 (FIG. 6). The head 33 is smooth, rounded and of variable size. The head 33 provides a surface area for the drop D to adhere to rather than adhere to and migrate along the external surface 28 of the dropper tip 30.

Figure 6A:
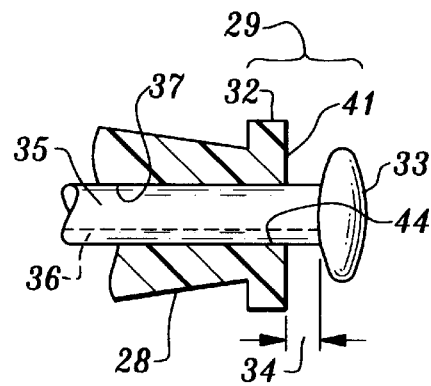
FIG. 6A is a detailed cross sectional view of the free end of the present invention.

The dropper tip 30 further includes an annulus 32 at the free end 29 of the tip 30 (FIGS. 6 and 6A). The annulus 32 encircles the external opening 44 of the internal passage 37 and the stem 35 at the free end 29 of the dropper tip 30. The annulus 32 may be excavated on its outer surface 39 (FIG. 6) or it may be flat 41 (FIG. 6A). The annulus 32 may be of variable size and provides a surface for a drop D of liquid 21 to adhere to while awaiting release. The annulus 32 furthermore forms a barrier against a drop D of liquid 21 from adhering to and migrating along the external surface 28 (FIGS. 6 and 6A) of the dropper tip 30.

The dropper tip 30 further includes a fissure 34 at the free end 29 of the tip 30 (FIG. 6). The fissure 34 is formed by a gap between the annulus 32 and the head 33 of the stem 35. The fissure 34 provides an area for the formation of a drop D and also for its retention until released. The fissure 34 creates a guide for the drop D as it falls from the free end 29 of the dropper tip 30 into an eye E.

Figure 7:
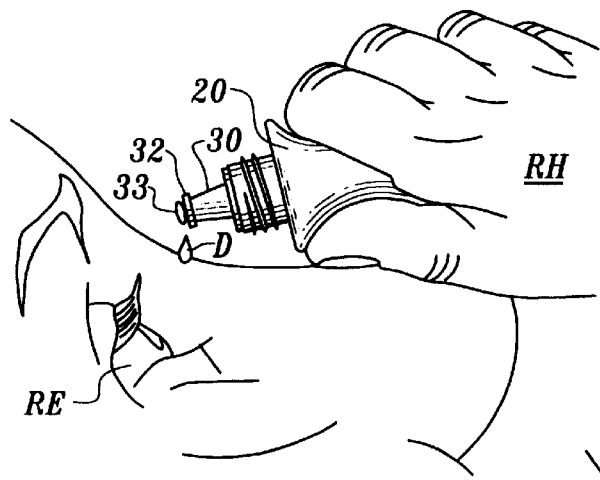
FIG. 7 is a side elevation demonstrating drop instillation into an eye while holding the present invention above and over an opened eye with the head tilted back.

As most clearly shown in FIG. 7, in use and operation, to instill an eye drop D into an eye E, the dropper bottle 20 is held in a horizontal orientation with the free end 29 of the dropper tip 30 aligned above and over an opened eye E. By compressing the walls 19 of the reservoir 20, the liquid 21 is forced into the hollowed-out 40 base 34 and into the internal opening 42 of the internal passage 37 (FIG. 6). The liquid 21 follows the groove 36 of the stem 35 and flows to the external opening 44 of the internal passage 37.

At the external opening 44 of the dropper tip 30, the liquid 21 forms into a drop D and adheres briefly to the surface of the annulus 32 and to the surface of the head 33 before falling. The external surface of the annulus 32 may be excavated 39 (FIG. 6) or it may be flat 41 (FIG. 6A). The adherence of the drop D between the annulus 32 and the head 33, which is a fissure 34, prevents the drop D from adhering to and migrating along the external surface 28 of the tip 30. When the drop D is of suffcient volume and weight, gravity causes the drop D to fall, being guided by the borders of the fissure 34. The patient need not rotate the bottle 20 in a marked vertically down manner to prevent the drop D from adhering to and migrating along the external surface 28 of the dropper tip 30.

Figure 8:
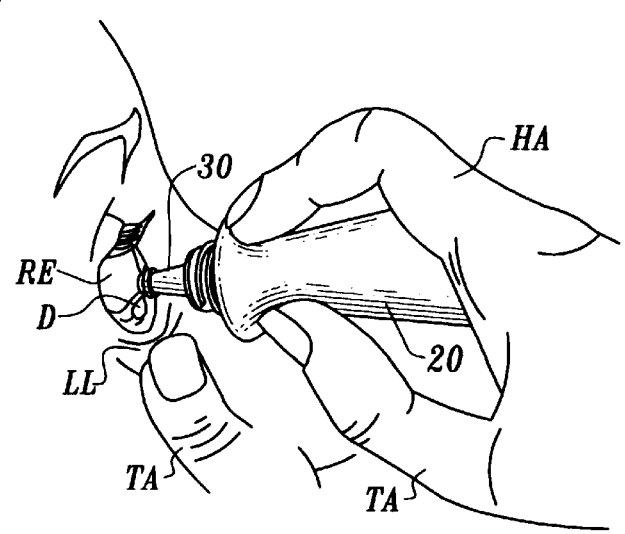
FIG. 8 is a side elevation demonstrating drop instillation in a created pocket of the lower eyelid by a caregiver, while the present invention is held from the side and below the line of vision in a near horizontal orientation.

FIG. 8 demonstrates an assistant retracting the outer, lower eyelid LL away from the eye E with his/her left thumb TA to create a pocket in the eyelid for the drop D to fall into. A bottle 20 is held in the caregiver's right hand HA in a near horizontal orientation from the patient's side rather than from straight in front and in the direct line of vision. This provides a much less threatening gesture to the patient and hence greater cooperation from the patient for instilling a drop D of liquid 21 into the eye E by a caregiver.

Figure 9:
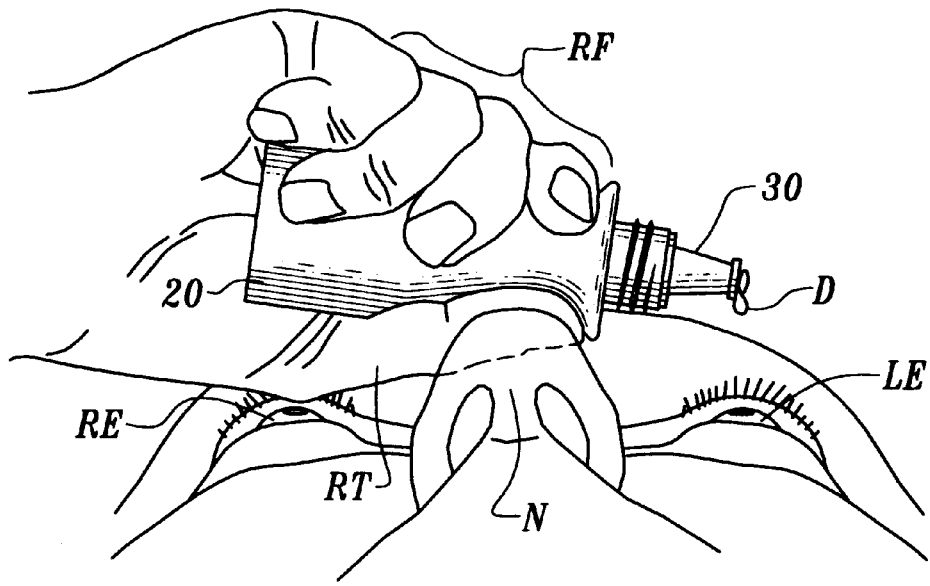
FIG. 9 is a view of the head tilted back and the eyes seen from below while a person demonstrates the instillation of a drop into the left eye using the right hand and with the present invention held in a near horizontal orientation.
Figure 10:
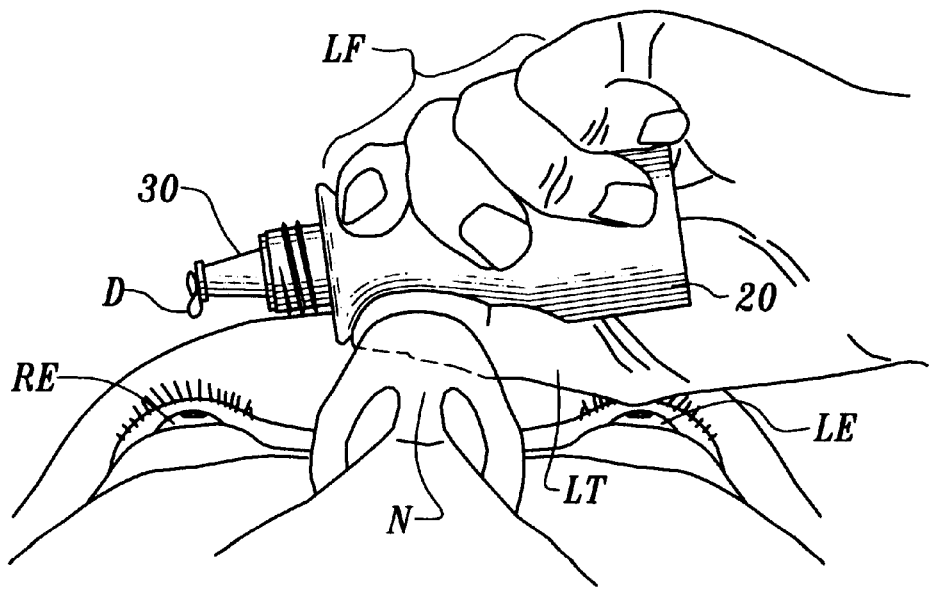
FIG. 10 is a view of the head tilted back and the eyes seen from below while a person demonstrates the instillation of a drop into the right eye using the left hand and with the present invention held in a near horizontal orientation.

FIGS. 9 and 10 demonstrate the bottle 20 being held in a near horizontal orientation and supported against the bridge of the nose N. This is especially important in those cases where the patient is unable to use the method shown in FIG. 7. In FIG. 9 is demonstrated a patient instilling a drop D of liquid 21 into the left eye LE with the right fingers RH and thumb RT. FIG. 10 shows a patient instilling a drop D of liquid 21 into the right eye RE with the left fingers LF and thumb LT. In both Figures, the bottle 20 and tip 30 may be held in a near horizontal orientation because the present invention discourages the drop D from adhering to and migrating along the external surface 28 of the dropper tip 30. The present invention does not require the dropper bottle 20 and the dropper tip 30 to be held vertically down over the eye E for instillation.

What is claimed is:

1. A dropper tip that enables a drop of liquid to fall precisely and consistently from a free end, even if the tip is held in a horizontal orientation, rather than adhere to and migrate along an external surface of the tip; the tip comprising in combination:

(a) a base opposite said free end of said tip for inserting into a liquid reservoir, the reservoir having compressible and resilient walls;

(b) an internal passage through said tip for said drops of liquid to flow externally from said reservoir when the walls of said reservoir are compressed.

2. The tip of claim 1 having an internal opening at said reservoir end of said internal passage;

(a) said internal opening connecting to a hollowed-out base of said tip.

3. The tip of claim 1 having an external opening at said free end of said internal passage.

4. The tip of claim 1 having an annulus at said free end of said tip;

(a) said annulus encircling said external opening of said internal passage;

(b) said annulus being of variable size.

5. The annulus of claim 4 having a flat or an excavated surface;

(a) said flat or said excavated surface forming an area for drop formation.

6. The annulus of claim 4 having a surface for adherence of said drop of liquid to said free end of said tip.

7. The annulus of claim 4 forming a barrier against said drop of liquid adhering to and migrating along said external surface of said tip.

8. The tip of claim 1 having a fissure at said free end of said tip;

(a) said fissure formed by a space between said head of said stem and said annulus of said tip;

(b) the width of said fissure being determined by the proximity of said head to said annulus;

(c) said fissure forming a cradle for drop formation;

(d) said fissure forming a guide for precise drop release.

\* \* \* \* \*